(12) United States Patent
Ohashi et al.

(10) Patent No.: US 7,141,249 B2
(45) Date of Patent: *Nov. 28, 2006

(54) RAPIDLY SOLUBLE DRUG COMPOSITION

(75) Inventors: Mamoru Ohashi, Amagasaki (JP); Kazuyoshi Ogasawara, Kitakatsuragi-gun (JP); Yoshimi Shirai, Suita (JP); Hiroshi Fujioka, Ibaraki (JP)

(73) Assignee: Dainippon Sumitomo Pharma Co., Ltd., Osaka-fu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/529,715

(22) PCT Filed: Oct. 15, 1998

(86) PCT No.: PCT/JP98/04658

§ 371 (c)(1),
(2), (4) Date: Apr. 19, 2000

(87) PCT Pub. No.: WO99/20277

PCT Pub. Date: Apr. 29, 1999

(65) Prior Publication Data

US 2002/0197308 A1    Dec. 26, 2002

(30) Foreign Application Priority Data

Oct. 20, 1997    (JP) .................................. 9-306635

(51) Int. Cl.
  *A61K 9/20*    (2006.01)
  *A61K 9/14*    (2006.01)
  *A61K 31/495*  (2006.01)
(52) U.S. Cl. .................... 424/465; 424/464; 424/489; 514/951; 514/960; 514/249

(58) Field of Classification Search ................ 514/249, 514/951, 960; 424/94.4, 400, 464, 465, 489, 424/451, 452, 470
See application file for complete search history.

(56) References Cited

U.S. PATENT DOCUMENTS

| 4,910,022 | A | * | 3/1990 | Bavitz et al. ............... 424/465 |
| 5,258,382 | A |   | 11/1993 | Negoro et al. ............. 514/249 |
| 5,356,636 | A | * | 10/1994 | Schneider et al. ........ 424/489 |
| 5,858,410 | A | * | 1/1999 | Muller et al. ............... 424/489 |
| 5,952,356 | A | * | 9/1999 | Ikeda et al. ................. 514/340 |
| 6,297,244 | B1 | * | 10/2001 | Ohashi et al. ............. 514/249 |
| 6,458,811 | B1 | * | 10/2002 | Arbuthnot et al. ........ 514/324 |

FOREIGN PATENT DOCUMENTS

JP    5-186472    4/1996

OTHER PUBLICATIONS

English Language Translation of the Document: "Design and Evaluation of Peroral Pharmaceutical Preparations (In Japanese)", edited by Mitsuru Hashida, Yakugyo Jihosya, Feb. 10, 1995, pp. 81-84, 168-171 (cited in the International Search Report of the original PCT/JP98/04658) thereof.

(Continued)

*Primary Examiner*—Sharmilla S. Gollamudi
(74) *Attorney, Agent, or Firm*—Wenderoth, Lind & Ponack, L.L.P.

(57) ABSTRACT

A fast-dissolving pharmaceutical composition comprising micronized (R)-2-(4-bromo-2-fluorobenzyl)-1,2,3,4-tetrahydropyrrolo[1,2-a]pyrazine-4-spiro-3'-pyrrolidine-1,2',3,5'-tetrone (hereinafter, referred to as AS-3201). The present pharmaceutical composition has improved dissolution characteristics as well as a good bioavailability.

5 Claims, 1 Drawing Sheet

OTHER PUBLICATIONS

English Language translation of the Document "Practical Drug Additives (In Japanese)", cited by Research Team Concerning Drug Additives, Mar. 5, 1974, pp. 215-217, 258-259 (cited in the International Search Report of the original PCT/JP98/04658) thereof.

Chemical Abstracts, 122, 9860 (1995) (English Abstract of JP-A-6-192222).

Chemical Abstracts, 125, 221569 (1996) (English Abstract of JP-A-8-176105).

J. Lutomski et al., "Postep W Technice Farmaceutyusznej", p. 102, 1981 (English translation also enclosed).

"Design and Evaluation of Peroral Pharmaceutical Preparations (in Japanese)", edited by Mitsuru Hashida, Yakygyo Jihosha, Feb. 10, 1995, pp. 81-84, 168-171, Trans. Sep. 20, 2000.

"Practical Drug Additives (in Japanese)", Research Team Concerning Drug Additives, Mar. 5, 1974, pp. 258-259, Trans Sep. 26, 2000.

\* cited by examiner

RAPIDLY SOLUBLE DRUG COMPOSITION

TECHNICAL FIELD

The present invention relates to a fast-dissolving pharmaceutical composition of (R)-2-(4-bromo-2-fluorobenzyl)-1,2,3,4-tetrahydropyrrolo[1,2-a]pyrazine-4-spiro-3'-pyrrolidine-1,2',3,5'-tetrone (hereinafter, referred to as "AS-3201") having a potent aldose reductase inhibitory activity.

BACKGROUND ART

AS-3201 is the compound of the following formula. Said compound is described in Example 22 of Japanese Patent No. 2516147 (U.S. Pat. No. 5,258,382), Reference Example 12 of JP-A-6-192222 (Chem. Abstr., 122, 9860 (1995)), and Experiment of JP-A-8-176105 (Chem. Abstr., 125, 221569 (1996)), and its potent aldose reductase inhibitory activities are disclosed therein.

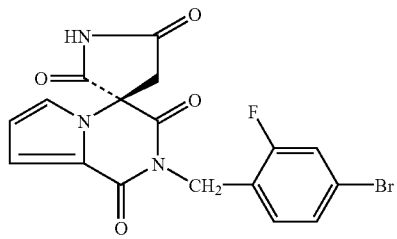

Example 28 of Japanese Patent No. 2516147 (USP 5258382) describes a method for preparing specific tablets of AS-3201. That is, it is described therein that AS-3201 (1 g), corn starch (25 g), lactose (58 g), crystalline cellulose (11 g), hydroxypropylcellulose (3 g), light anhydrous silicic acid (1 g) and magnesium stearate (1 g) are blended, granulated and made into 1,000 tablets each weighing 100 mg by a conventional method.

During the studies on methods for preparing AS-3201-containing pharmaceutical compositions having an excellent bioavailability, the present inventors have found that the water-solubility of said substance is extremely low in the range of low pH to the extent of several μg/ml, and therefore, the plasma concentration of AS-3201 varies widely among the individuals to be administered.

Under such circumstances, the present inventors have further intensively studied, and have found that by using micronized AS-3201 in a composition, the dissolution characteristics of said substance from the composition are remarkably improved, and as a result, an AS-3201-containing fast-dissolving pharmaceutical composition having a good bioavailability can be obtained, and finally have accomplished the present invention.

DISCLOSURE OF INVENTION

The present invention provides a fast-dissolving pharmaceutical composition comprising micronized AS-3201.

The terms used in the present specification are explained below.

The "micronized AS-3201" means powders of AS-3201 having a mean particle size of less than about 20 μm. The "mean particle size" means a particle size of being at 50% in cumulative particle distribution on weight or volume basis (ref., HA Lieberman et al., "Pharmaceutical Dosage Forms: Tablets", Marcel Dekker, Inc., New York, 1990, vol. 2, 174–186; Kouichi IINOYA (edit.) "Handbook of Powder and Particle Measurement (in Japanese)", The NIKKAN KOGYO SHINBUN LTD., 1981, 29–36). The "dissolution test" means a test in which the dissolution of AS-3201 from test pharmaceutical compositions in an amount corresponding to 20 mg of AS-3201 is evaluated according to Paddle method (50 rpm) specified in the Twelfth Edition of the Pharmacopoeia of Japan, using a 0.2 M phosphate buffer (pH 6.5, 900 ml) as a test solution, and assaying AS-3201 by spectrophotometry at 300 nm. The "$pK_{a1}$" means an acid dissociation exponent of an acidic substance at 25° C. in an infinitely diluted solution thereof. When an acidic substance is a polybasic acid, it means an acid dissociation exponent at the first step of dissociation. The "water-solubility" means a maximum amount of a solute being dissolved in 100 ml of water. The term "about" is used with the intention of including values following said term.

The mean particle size of the micronized AS-3201 is preferably less than about 10 um, more preferably less than about 5 μm, and most preferably in the range of about 0.5 um to about 3 μm.

According to the method disclosed in Japanese Patent No. 2516147 (U.S. Pat. No. 5,258,382), crystals of AS-3201 having a mean particle size of about 60 μm to about 120 μm can usually be obtained. The micronization of AS-3201 crystals is carried out using a mill that is conventionally used in the pharmaceutical field. Mills are, for example, a fluid energy mill such as Jet Mill (manufactured by SEISHIN ENTERPRISE Co., LTD., Japan), a high speed rotative impact mill such as Sample Mill (manufactured by Hosokawa Micron Corporation, Japan), Pin Mill (manufactured by ALPINE, Germany), or Angmill (manufactured by Hosokawa Micron Corporation, Japan), a wet form high speed tumbling trituration mill such as MICROS (manufactured by Nara Machinery Co., Ltd., Japan), and a tumbling mill such as a ball mill. In order to obtain micronized powders having a mean particle size of less than about 5 μm, a fluid energy mill is preferably used. The micronization can be carried out on AS-3201 crystals alone, or on a mixture of AS-3201 crystals and a part or whole of pharmaceutical excipients or carriers, which are used in the preparation of pharmaceutical compositions.

The AS-3201-containing fast-dissolving pharmaceutical composition of the present invention may be solid dosage forms, and includes, for example, tablets, capsules, granules, powders, etc. These pharmaceutical compositions can be prepared by mixing micronized AS-3201 with pharmaceutical excipients or carriers such as diluents, disintegrators, binders and lubricants by a conventional method. For example, the mixture is granulated by wet-granulation such as high-shear granulation, fluid bed granulation, agitation fluid bed granulation, centrifugal fluid bed granulation, or extrusion granulation, or by dry-granulation such as roller compaction or slugging, and then the resulting granules are put into capsules for capsule preparations, or compressed for tablet preparations. Alternatively, a mixture of micronized AS-3201 and pharmaceutical excipients or carriers can directly be put into capsules for capsule preparations, or compressed for tablet preparations. These pharmaceutical compositions may optionally be coated, or may additionally contain stabilizers, surfactants, coloring agents, flavoring agents, etc.

The pharmaceutical excipients or carriers may be any ones except for ones showing a bad compatibility with AS-3201. The diluents include, for example, lactose, starch, crystalline cellulose, D-mannitol, sucrose, glucose, erythritol, xylitol, D-sorbitol, anhydrous dibasic calcium phosphate, and calcium sulfate. The disintegrators are, for example, starch, crystalline cellulose, low substituted hydroxypropylcellulose, carmellose, carmellose calcium, sodium carboxymethyl starch, croscarmellose sodium, partly pregelatinized starch, and hydroxypropyl starch. The binders are, for example, acacia, starch, hydroxypropylcellulose, hydroxypropylmethylcellulose, polyvinyl alcohol, pullulan, gelatin, ethylcellulose, methylcellulose, carmellose sodium, and dextrin. The lubricants are, for example, magnesium stearate, calcium stearate, stearic acid, sucrose esters of fatty acids, light anhydrous silicic acid, talc, hydrogenated oil, and macrogol.

The stabilizer may be any pharmaceutically acceptable acidic substances having an acidity more potent than that of AS-3201, i.e., $pK_a$=5.6–5.8, and preferable acidic substances are ones having a $pK_{a1}$ of less than about 4.5 and a water-solubility of larger than about 10 g/100 ml at 15° C.–25° C. More preferable acidic substances are ones having a $pK_{a1}$ of less than about 3.3 and a water-solubility of larger than about 50 g/100 ml at 15° C.–25° C. Especially preferable acidic substances are, for example, citric acid, tartaric acid, maleic acid, and phosphoric acid. Among these acidic substances, tartaric acid is most preferable. The content of the acidic substance is preferably in the range of about 0.5% by weight to about 2.5% by weight. It is preferable to add a stabilizer in the case of preparing a pharmaceutical composition containing AS-3201 in a ratio of less than about 5% by weight.

The surfactants to be used in the present pharmaceutical composition are, for example, sorbitan fatty acid esters and polysorbates. The coloring agents are, for example, tar color, caramel, and red iron oxide. The flavoring agents are, for example, sweeteners and perfumes.

The dissolution characteristics of the active substance from the composition can be remarkably improved by using micronized AS-3201, and by further controlling the combination ratio of pharmaceutical excipients or carriers, AS-3201-containing fast-dissolving pharmaceutical compositions having more improved dissolution characteristics as well as good bioavailability can be obtained. The combination ratio of the pharmaceutical excipients or carriers may vary depending on the content of AS-3201. The content of AS-3201 in the present fast-dissolving pharmaceutical composition is usually in the range of about 0.5% by weight to about 25% by weight, to the total weight of the pharmaceutical composition. When the content of AS-3201 is in the range of about 0.5% by weight to 5% by weight to the total weight of the pharmaceutical composition, then the pharmaceutical composition usually comprises a diluent in a ratio of about 51% by weight—about 93.8% by weight, a disintegrator in a ratio of about 5% by weight—about 35% by weight, a binder in a ratio of about 0.5% by weight—about 5% by weight, and a lubricant in a ratio of about 0.2% by weight—about 4% by weight. More preferably, the pharmaceutical composition comprises a diluent in a ratio of about 59% by weight—about 88% by weight, a disintegrator in a ratio of about 10% by weight—about 30% by weight, a binder in a ratio of about 1% by weight—about 3% by weight, and a lubricant in a ratio of about 0.5% by weight—about 3% by weight. When the content of AS-3201 is more than 5% by weight and less than about 25% by weight to the total weight of the pharmaceutical composition, then the present composition usually comprises a diluent in a ratio of about 16% by weight—about 84.3% by weight, a disintegrator in a ratio of about 10% by weight—about 50% by weight, a binder in a ratio of about 0.5% by weight—about 5% by weight, and a lubricant in a ratio of about 0.2% by weight—about 4% by weight, and more preferably, a diluent in a ratio of about 29% by weight—about 73.5% by weight, a disintegrator in a ratio of about 20% by weight—about 40% by weight, a binder in a ratio of about 1% by weight—about 3% by weight, and a lubricant in a ratio of about 0.5% by weight—about 3% by weight.

Since AS-3201 has an extremely low water-solubility to the extent of several μg/ml in the range of low pH, there is a correlation between the initial dissolution rate and the bioavailability of AS-3201-containing pharmaceutical compositions, and compositions having a better initial dissolution rate can show a better bioavailability. From the viewpoint of the above, preferable compositions are ones having a dissolution percentage of the active substance of 50% or more for 15 minutes after the start of the dissolution test, and more preferable pharmaceutical compositions are ones having a dissolution percentage of the active substance of 80% or more for 15 minutes after the start of the dissolution test.

The AS-3201-containing fast-dissolving pharmaceutical composition of the present invention may be packed in a bottle using materials of low moisture-permeability or in damp-proof packages such as heat-sealed packages, if necessary.

BEST MODE FOR CARRYING OUT THE INVENTION

Figure 1:
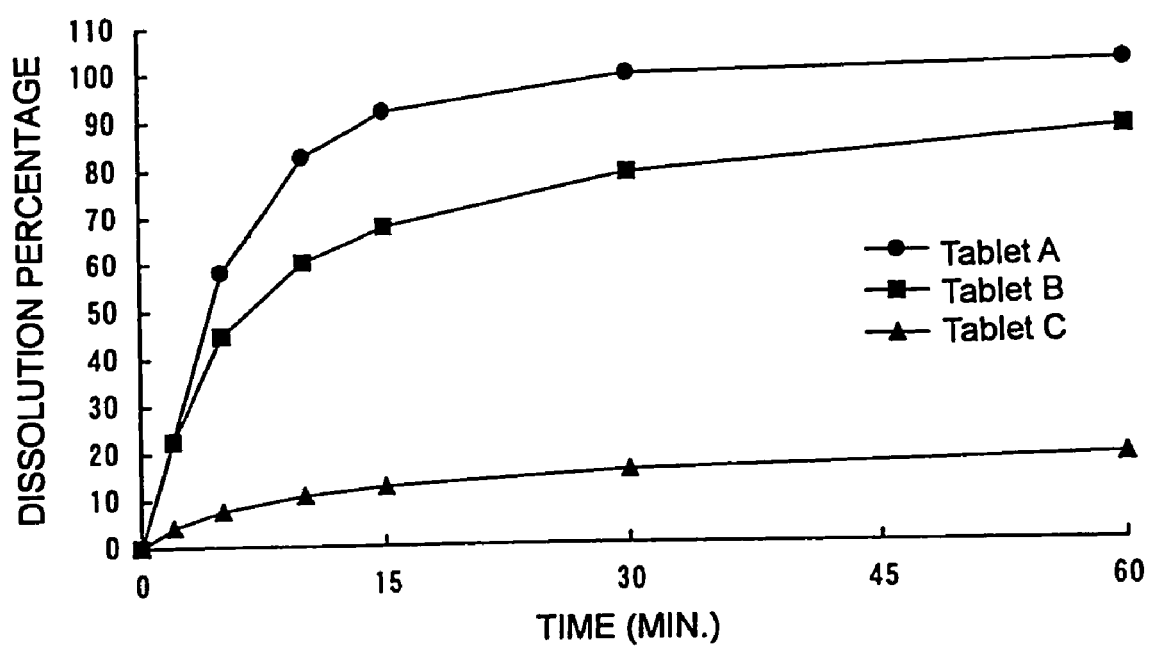
FIG. 1 is a graph showing a dissolution pattern of the tablets of Examples 1 and 2, and Comparative Example 1.

The present invention is illustrated in more detail by Examples and Comparative Example, but the present invention should not be construed to be limited thereto. The mean particle size was measured using a laser diffraction particle size distribution analyzer (HELOS & RODOS (trademark), manufactured by SYMPATEC GmbH, Germany), and calculated from cumulative particle distribution on volume basis by dry air dispersion method (dispersion air pressure: 0.5 atm).

EXAMPLE 1

| Preparation of tablets: | |
|---|---|
| AS-3201 | 160 g |
| Tartaric acid | 8 g |
| Lactose | 492 g |
| Low substituted hydroxypropylcellulose | 300 g |
| Hydroxypropylcellulose | 20 g |
| Magnesium stearate | 20 g |
| Total | 1000 g |

AS-3201 crystals were micronized using Single Truck Jet Mill (manufactured by SEISHIN ENTERPRISE CO., LTD., hereinafter abbreviated as "Jet Mill") with compression air pressure of 6 kgf/cm² to give powders having a mean particle size of about 1.5 μm. The micronized AS-3201 powders thus obtained, lactose, and low substituted hydroxypropylcellulose were charged into a fluid bed granulator and drier, and then the mixture was granulated by spraying thereto a solution of tartaric acid in a 5% aqueous hydroxypropylcellulose solution. The granules were dried, and thereto was added magnesium stearate, and the mixture was blended in a V-blender. The resultant was compressed on a rotary tableting machine to give tablets weighing 125 mg and containing 20 mg of AS-3201 each.

EXAMPLE 2

Preparation of Tablets:

AS-3201 crystals were micronized by Sample Mill (manufactured by Hosokawa Micron Corporation) to give powders having a mean particle size of about 10 μm. The micronized AS-3201 powders thus obtained were granulated, dried and compressed in the same manner as in Example 1, to give tablets weighing 125 mg and containing 20 mg of AS-3201 each.

COMPARATIVE EXAMPLE 1

Preparation of Tablets:

Non-micronized AS-3201 crystals having a mean particle size of about 87 μm were granulated, dried and compressed in the same manner as in Example 1, to give tablets weighing 125 mg and containing 20 mg of AS-3201 each.

EXPERIMENT 1

Dissolution Test:

The dissolution of the active substance from the tablets obtained in Examples 1 and 2 and Comparative Example 1 was evaluated according to Paddle method (50 rpm) specified in the Twelfth Edition of the Pharmacopoeia of Japan, using a 0.2 M phosphate buffer (pH 6.5, 900 ml) as a test solution. The quantitative assay of AS-3201 was carried out by spectrophotometry at 300 nm.

The results are shown in FIG. 1. Each point of FIG. 1 shows the mean value of the results in three repeats of the experiments on each tablet of Example 1, Example 2 and Comparative Example 1.

As is shown in FIG. 1, the tablets of Example 1 and Example 2 show remarkably improved dissolution characteristics, as compared with the tablets of Comparative Example 1.

EXAMPLE 3

| Preparation of tablets: | |
| --- | --- |
| AS-3201 | 160 g |
| Tartaric acid | 10 g |
| Lactose | 600 g |
| Low substituted hydroxypropylcellulose | 200 g |
| Hydroxypropylcellulose | 20 g |
| Magnesium stearate | 10 g |
| Total | 1000 g |

The above components were treated in the same manner as in Example 1, and compressed to give tablets weighing 125 mg and containing 20 mg of AS-3201 each. The dissolution percentage of the active substance from the tablets thus obtained for 15 minutes after the start of the dissolution test was 72.6%.

EXAMPLE 4

| Preparation of tablets: | |
| --- | --- |
| AS-3201 | 20 g |
| Tartaric acid | 8 g |
| Lactose | 732 g |
| Low substituted hydroxypropylcellulose | 200 g |
| Hydroxypropylcellulose | 20 g |
| Magnesium stearate | 20 g |
| Total | 1000 g |

AS-3201 crystals were micronized using Jet Mill with compression air pressure of 6 kgf/cm$^2$, and the resultant was charged into a fluid bed granulator and drier together with lactose and low substituted hydroxypropylcellulose, and then, the resultant was granulated by spraying thereto a solution of tartaric acid in a 5% aqueous hydroxypropylcellulose solution. The granules were dried, and thereto was added magnesium stearate, and the mixture was blended in a V-blender. The resultant was compressed on a rotary tableting machine to give tablets weighing 125 mg and containing 2.5 mg of AS-3201 each.

The dissolution percentage of the active substance from the tablets thus obtained for 15 minutes after the start of the dissolution test was 93.0%.

EXAMPLE 5

| Preparation of tablets: | |
| --- | --- |
| AS-3201 | 80 g |
| Tartaric acid | 4 g |
| Lactose | 246 g |
| Low substituted hydroxypropylcellulose | 150 g |
| Hydroxypropylcellulose | 10 g |
| Magnesium stearate | 10 g |
| Total | 500 g |

AS-3201 crystals were micronized using Jet Mill with compression air pressure of 6 kgf/cm$^2$, and thereto were added lactose and low substituted hydroxypropylcellulose, and then, the resulting mixture was blended in a Versatile Mixer for 5 minutes. To the mixture was added a solution of tartaric acid in a 4% aqueous hydroxypropylcellulose solution, and the mixture was further kneaded for 10 minutes. The mixture was dried, and thereto was added magnesium stearate, and the resulting mixture was compressed on a single-punch tableting machine to give tablets weighing 125 mg and containing 20 mg of AS-3201 each.

The dissolution percentage of the active substance from the tablets thus obtained for 15 minutes after the start of the dissolution test was 93.2%.

EXAMPLE 6

Preparation of tablets:

| | |
|---|---|
| AS-3201 | 144 g |
| Lactose | 549 g |
| Low substituted hydroxypropylcellulose | 180 g |
| Hydroxypropylcellulose | 18 g |
| Magnesium stearate | 9 g |
| Total | 900 g |

AS-3201 crystals were micronized using Jet Mill with compression air pressure of 6 kgf/cm$^2$, and the resultant was put into a fluid bed granulator and drier together with lactose and low substituted hydroxypropylcellulose, and then, the mixture was granulated by spraying thereto a 5% aqueous hydroxypropylcellulose solution. After drying, to the granules was added magnesium stearate, and the mixture was blended in a V-blender. The resultant was compressed on a rotary tableting machine to give tablets weighing 125 mg and containing 20 mg of AS-3201 each.

The dissolution percentage of the active substance from the tablets thus obtained for 15 minutes after the start of the dissolution test was 92.0%.

EXAMPLES 7–9

Preparation of tablets:

| | Ex. 7 | Ex. 8 | Ex. 9 |
|---|---|---|---|
| AS-3201 | 40 g | 40 g | 40 g |
| Tartaric acid | 8 g | 8 g | 8 g |
| Lactose | 712 g | 672 g | 632 g |
| Low substituted hydroxypropylcellulose | 200 g | 240 g | 280 g |
| Hydroxypropylcellulose | 20 g | 20 g | 20 g |
| Magnesium stearate | 20 g | 20 g | 20 g |
| Total | 1000 g | 1000 g | 1000 g |

AS-3201 micronized using Jet Mill was granulated, dried and compressed in the same manner as in Example 1 to give tablets weighing 125 mg and containing 5 mg of AS-3201 each.

The dissolution percentages of the active substance from the tablets of Examples 7, 8 and 9 for 15 minutes after the start of the dissolution test were 91.0%, 94.5% and 92.7%, respectively.

EXAMPLES 10–12

Preparation of tablets:

| | Ex. 10 | Ex. 11 | Ex. 12 |
|---|---|---|---|
| AS-3201 | 80 g | 80 g | 80 g |
| Tartaric acid | 8 g | 8 g | 8 g |
| Lactose | 672 g | 632 g | 592 g |
| Low substituted hydroxypropylcellulose | 200 g | 240 g | 280 g |
| Hydroxypropylcellulose | 20 g | 20 g | 20 g |
| Magnesium stearate | 20 g | 20 g | 20 g |
| Total | 1000 g | 1000 g | 1000 g |

AS-3201 micronized using Jet Mill was granulated, dried and compressed in the same manner as in Example 1 to give tablets weighing 125 mg and containing 10 mg of AS-3201 each.

The dissolution percentages of the active substance from the tablets of Examples 10, 11 and 12 for 15 minutes after the start of the dissolution test were 89.4%, 91.6% and 92.2%, respectively.

INDUSTRIAL APPLICABILITY

As explained above, the AS-3201-containing fast-dissolving pharmaceutical composition of the present invention has improved dissolution characteristics as well as a good bioavailability.

The invention claimed is:

1. A fast-dissolving pharmaceutical composition in a solid dosage form, comprising micronized (R)-2-(4-bromo-2-fluorobenzyl)-1,2,3,4-tetrahydropyrrolo[1,2-a]pyrazine-4-spiro-3'-pyrrolidine-1,2',3,5'-tetrone (hereinafter referred to as "AS-3201") having a mean particle size of in a range of about 1.5 μm to less than about 10 μm in a ratio of about 0.5% by weight to about 25% by weight of the total weight of the pharmaceutical composition, and as a stabilizer at least one acidic substance having a pKa less than about 5.6,
wherein the acidic substance is a member selected from the group consisting of citric acid, tartaric acid, maleic acid, and phosphoric acid, and
wherein when in a dissolution percentage of AS-3201 from the composition is measured according to the Paddle method, 50% or more of the AS-3201 in the composition is dissolved with 15 minutes from the start of the method.

2. The fast-dissolving pharmaceutical composition according to claim 1, wherein the mean particle size of the micronized AS-3201 is in the range of about 1.5 μm to about 5 pin.

3. The fast-dissolving pharmaceutical composition according to claim 1, wherein the mean particle size of the micronized AS-3201 is in the range of about 1.5 μm to about 3 μm.

4. The fast-dissolving pharmaceutical composition according to claim 1, wherein the solid dosage form is tablets, capsules, granules or powder.

5. The fast-dissolving pharmaceutical composition according to claim 1, wherein the acidic substance is tartaric acid.

* * * * *

UNITED STATES PATENT AND TRADEMARK OFFICE
CERTIFICATE OF CORRECTION

PATENT NO.       : 7,141,249 B2
APPLICATION NO.  : 09/529715
DATED            : November 28, 2006
INVENTOR(S)      : Mamoru Ohashi et al.

It is certified that error appears in the above-identified patent and that said Letters Patent is hereby corrected as shown below:

Column 8, claim 2, line 52, please change "5 pin" to -- 5 μm --.

Signed and Sealed this

Sixth Day of February, 2007

JON W. DUDAS
*Director of the United States Patent and Trademark Office*